US00PP21259P2

(12) United States Plant Patent
Barends

(10) Patent No.: US PP21,259 P2
(45) Date of Patent: Aug. 31, 2010

(54) ***GERANIUM* PLANT NAMED 'FIPELDANLAV'**
(50) Latin Name: *Pelargonium peltatum*
Varietal Denomination: Fipeldanlav

(75) Inventor: Eveline Barends, De Lier (NL)

(73) Assignee: Fides B.V., DeLier (NL)

( * ) Notice: Subject to any disclaimer, the term of this patent is extended or adjusted under 35 U.S.C. 154(b) by 0 days.

(21) Appl. No.: 12/383,285

(22) Filed: Mar. 23, 2009

(51) Int. Cl.
*A01H 5/00* (2006.01)

(52) U.S. Cl. ..... Plt./332

(58) Field of Classification Search ..... Plt./332
See application file for complete search history.

*Primary Examiner*—Susan B McCormick Ewoldt
(74) *Attorney, Agent, or Firm*—C. A. Whealy

(57) ABSTRACT

A new and distinct cultivar of Ivy *Geranium* plant named 'Fipeldanlav', characterized by its upright to outwardly spreading plant habit; freely basal branching habit; early and freely flowering habit; double lavender-colored flowers with red purple-colored venation; and good garden performance.

1 Drawing Sheet

Botanical designation: *Pelargonium peltatum.*
Cultivar denomination: 'FIPELDANLAV'.

BACKGROUND OF THE INVENTION

The present invention relates to a new and distinct cultivar of Ivy *Geranium* plant, botanically known as *Pelargonium peltatum*, and hereinafter referred to by the name 'Fipeldanlav'.

The new Ivy *Geranium* plant is a product of a planned breeding program conducted by the Inventor in De Lier, The Netherlands. The objective of the breeding program is to create new freely-branching and freely-flowering Ivy *Geranium* cultivars with large double flowers and attractive foliage and flower coloration.

The new Ivy *Geranium* plant originated from a cross-pollination made by the Inventor in De Lier, The Netherlands of two unnamed selections of *Pelargonium peltatum*, not patented. The new Ivy *Geranium* was discovered and selected by the Inventor as a single flowering plant from within the progeny of the stated cross-pollination in a controlled greenhouse environment in De Lier, The Netherlands in March, 2003.

Asexual reproduction of the new Ivy *Geranium* plant by vegetative terminal cuttings in a controlled greenhouse environment in De Lier, The Netherlands, since July, 2003, has shown that the unique features of this new Ivy *Geranium* plant are stable and reproduced true to type in successive generations.

SUMMARY OF THE INVENTION

Plants of the new Ivy *Geranium* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Fipeldanlav'. These characteristics in combination distinguish 'Fipeldanlav' as a new and distinct cultivar of Ivy *Geranium:*

1. Upright to outwardly spreading plant habit.
2. Freely basal branching habit.
3. Early and freely flowering habit.

4. Double lavender-colored flowers with red purple-colored venation.
5. Good garden performance.

Plants of the new Ivy *Geranium* differ primarily from plants of the parent selections in growth habit and plant habit as plants of the new Ivy *Geranium* are more vigorous in growth habit and more uniform in plant habit than plants of the parent selections.

Plants of the new Ivy *Geranium* can be compared to plants of *Pelargonium peltatum* 'Merifestival', disclosed in U.S. Plant Pat. No. 10,288. In side-by-side comparisons conducted in De Lier, The Netherlands, plants of the new Ivy *Geranium* differed from plants of 'Merifestival' in the following characteristics:

1. Plants of the new Ivy *Geranium* flowered earlier than plants of 'Merifestival'.
2. Plants of the new Ivy *Geranium* had darker-colored flowers than plants of 'Merifestival'.

Plants of the new Ivy *Geranium* can also be compared to plants of *Pelargonium peltatum* 'Tocana Teske', not patented. In side-by-side comparisons conducted in De Lier, The Netherlands, plants of the new Ivy *Geranium* differed from plants of 'Tocana Teske' in the following characteristics:

1. Plants of the new Ivy *Geranium* flowered earlier than plants of 'Tocana Teske'.
2. Plants of the new Ivy *Geranium* had lighter-colored flowers than plants of 'Tocana Teske'.

BRIEF DESCRIPTION OF THE PHOTOGRAPH

The accompanying colored photograph illustrates the overall appearance of the new Ivy *Geranium* plant, showing the colors as true as it is reasonably possible to obtain in colored reproductions of this type.

Colors in the photograph may differ slightly from the color values cited in the detailed botanical description which accurately describe the colors of the new Ivy *Geranium.*

The photograph comprises a side perspective view of a typical flowering plant of 'Fipeldanlav' grown in a container.

DETAILED BOTANICAL DESCRIPTION

The aforementioned photograph and following observations, measurements and values describe plants grown in De Lier, The Netherlands in a glass-covered greenhouse during the summer and under conditions which closely approximate commercial Ivy *Geranium* production. During the production of the plants day temperatures ranged from 17° C. to 18° C. and night temperatures ranged from 14° C. to 16° C. Plants were 13 weeks old when the photographs and the description were taken. In the detailed description, color references are made to The Royal Horticultural Society Colour Chart, 2001 Edition, except where general terms of ordinary dictionary significance are used.

Botanical classification: *Pelargonium peltatum* 'Fipeldanlav'.

Parentage:

*Female, or seed, parent.*—Unnamed selection of *Pelargonium peltatum,* not patented.

*Male or pollen parent.*—Unnamed selection of *Pelargonium peltatum*, not patented.

Propagation:

*Type.*—By vegetative terminal cuttings.

*Time to initiate roots, summer.*—About four days at temperatures of 22° C.

*Time to initiate roots, winter.*—About one week at temperatures of 22° C.

*Time to produce a rooted young plant, summer.*—About 16 days at temperatures of 22° C. to 30° C.

*Time to produce a rooted young plant, winter.*—About three weeks at temperatures of 20° C. to 25° C.

*Root description.*—Medium in thickness, fibrous; whitish grey in color.

*Rooting habit.*—Moderately freely branching, moderately dense.

Plant description:

*General appearance.*—Upright to outwardly spreading and eventually trailing plant habit; uniformly mounded; densely foliated.

*Growth and branching habit.*—Moderately vigorous growth habit. Freely basal branching habit with about four to five lateral branches per plant.

*Plant height, to top of umbels.*—About 14 cm to 16 cm.

*Plant height, to top of leaves.*—About 6 cm to 9 cm.

*Plant width.*—About 30 cm.

*Lateral branches.*—Length: About 13 cm to 20 cm. Diameter: About 3 mm to 6 mm. Internode length: About 3 cm to 6 cm. Texture: Pubescent. Strength: Moderately strong. Color: Close to 144C.

Foliage description:

*Arrangement.*—Alternate; simple.

*Length.*—About 5 cm to 7 cm.

*Width.*—About 9 cm.

*Shape.*—Roughly orbicular; palmately lobed.

*Apex.*—Acute.

*Base.*—Cordate; open.

*Margin.*—Entire.

*Venation pattern.*—Palmate.

*Texture, upper and lower surfaces.*—Smooth, glabrous.

*Color.*—Developing and fully expanded leaves, upper surface: Close to N137A; venation, close to 137D; zonation pattern, close to 177A. Developing and fully expanded leaves, lower surface: Close to 137C; venation, close to 137C. Petiole: Length: About 5 cm to 6 cm. Diameter: About 2 mm to 3 mm. Texture, upper and lower surfaces: Smooth, glabrous. Color, upper and lower surfaces: Close to 146B.

Flower description:

*Flower arrangement.*—Double flowers arranged in rounded hemispherical umbels arising from apical leaf axils. Umbels displayed above the foliage on strong peduncles. Flowers face upright to outward.

*Fragrance.*—None detected.

*Quantity of flowers.*—Freely flowering habit; about 18 to 28 flowers and flower buds per umbel.

*Flowering season.*—In De Lier, The Netherlands, flowering is continuous from late spring until frost in the autumn. Plants begin flowering about six to eight weeks after planting.

*Flower longevity.*—Individual flowers last about 2 to 14 days on the plant; flowers persistent.

*Umbel height.*—About 6 cm.

*Umbel diameter.*—About 8 cm to 10 cm.

*Flower diameter.*—About 5 cm.

*Flower depth* (*height*).—About 1 cm to 1.5 cm.

*Flower buds.*—Length: About 1 cm to 2 cm. Diameter: About 5 mm to 10 mm. Shape: Broadly elliptic. Color: Close to 146A.

*Petals.*—Quantity per flower: About ten to twelve. Length: About 2.3 cm to 2.5 cm. Width: About 1.5 cm to 1.7 cm. Shape: Lanceolate to ovate. Apex: Obtuse. Base: Attenuate. Margin: Entire. Texture, upper and lower surfaces: Smooth, glabrous. Color: When opening and fully opened, upper surface: Close to 76A; venation, close to 61A. Color becoming closer to 75A with development. When opening and fully opened, lower surface: Close to 76B; venation, close to 75B.

*Petaloids.*—Quantity per flower: If present, up to five. Length: About 1 cm to 1.5 cm. Width: About 1 cm to 1.5 mm. Shape: Narrowly ovate to irregularly oblanceolate. Apex: Obtuse. Base: Attenuate. Margin: Entire. Texture, upper and lower surfaces: Smooth, glabrous. Color: When opening and fully opened, upper surface: Close to 76A. When opening and fully opened, lower surface: Close to 76B.

*Sepals.*—Quantity per flower/arrangement: Five in a single whorl. Length: About 1 cm. Width: About 4 mm. Shape: Lanceolate. Apex: Acute. Base: Cuneate. Margin: Entire. Texture, upper and lower surfaces: Smooth, glabrous. Color, upper and lower surfaces: Close to N137A.

*Peduncle* (*umbel stem*).—Length: About 15 cm to 21 cm. Diameter: About 3 mm to 4 mm. Strength: Strong. Angle: Erect to about 30° C. from vertical. Texture: Smooth, glabrous. Color: Close to 146A.

*Pedicel* (*individual flower stem*).—Length: About 2 cm. Diameter: About 2 mm. Strength: Moderately strong. Angle: Erect to about 60° C. from vertical. Texture: Smooth, glabrous. Color: Close to 144A.

*Reproductive organs.*—Androecium: Stamen quantity per flower: If present, up to eight. Filament length: About 7 mm. Filament color: Close to 155A. Anther length: About 2 mm. Anther shape: Oblong. Anther color: Close to 202A. Pollen amount: Moderate. Pollen color: Close to 172C. Gynoecium: Pistil quantity per flower: One. Pistil length: About 1 cm to 1.5 cm. Stigma shape: Tapering; reflexed. Stigma color: Close to 64A. Style length: About 3 mm. Style color: Close to 64A. Ovary color: Close to 64A.

*Fruits/seeds.*—Fruit and seed development have not been observed.

Disease/pest resistance: Plants of the new Ivy *Geranium* have not been observed to be resistant to pathogens and pests common to Ivy *Geraniums.*

Garden performance: Plants of the new Ivy *Geranium* have been observed to tolerate rain, wind and temperatures ranging from about 0° C. to about 40° C. and have demonstrated good garden performance.

It is claimed:

1. A new and distinct Ivy *Geranium* plant named 'Fipeldanlav' as illustrated and described.

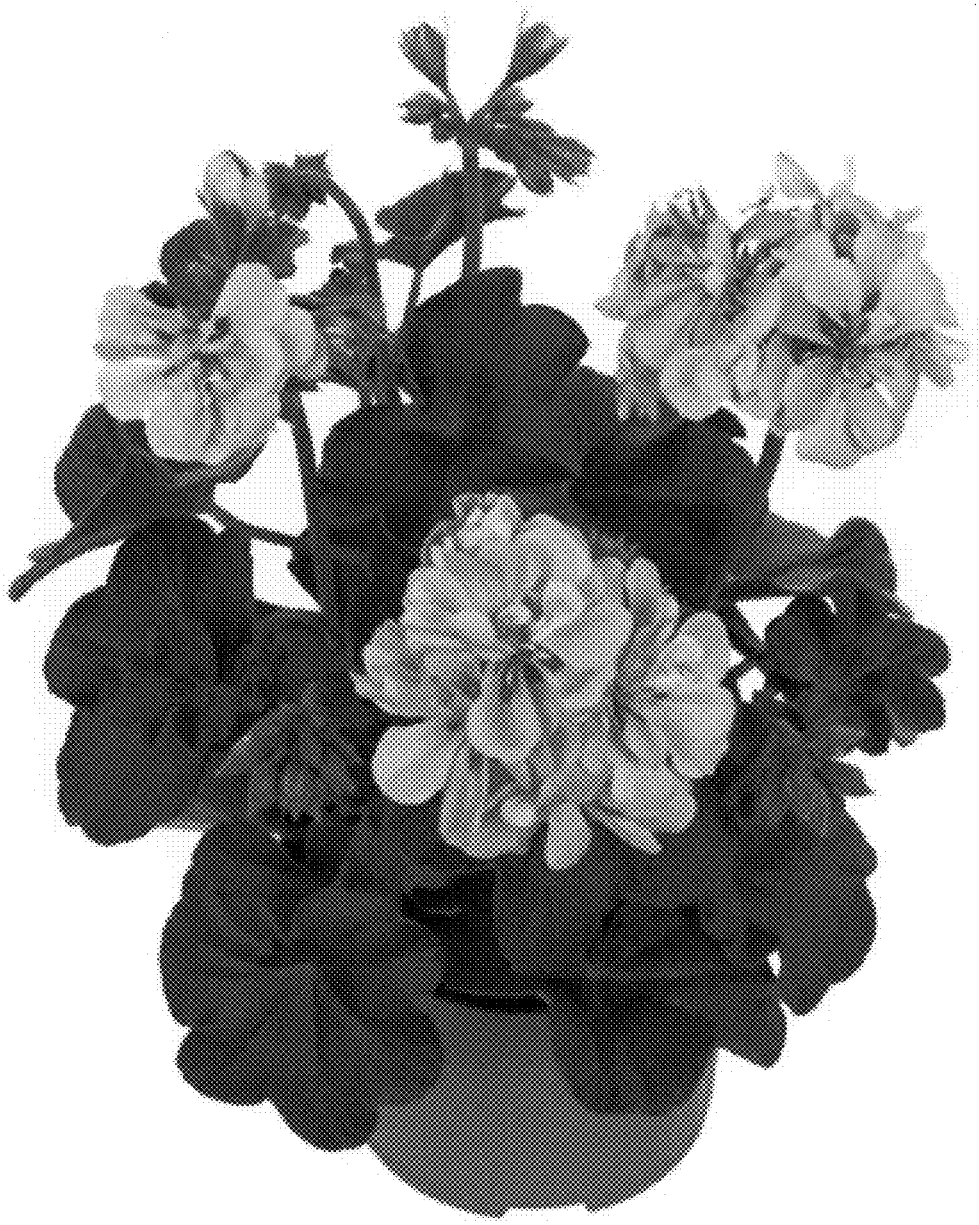

* * * * *